United States Patent

Melgaard et al.

[11] Patent Number: 6,048,493
[45] Date of Patent: *Apr. 11, 2000

[54] STERILIZABLE PASSAGEWAY

[75] Inventors: Hans Melgaard, North Oaks; Joseph Stitz, Cambridge, both of Minn.

[73] Assignee: Despatch Industries, Inc., Minneapolis, Minn.

[*] Notice: This patent issued on a continued prosecution application filed under 37 CFR 1.53(d), and is subject to the twenty year patent term provisions of 35 U.S.C. 154(a)(2).

[21] Appl. No.: 09/053,336

[22] Filed: Apr. 1, 1998

[51] Int. Cl.⁷ .................................................. A61L 2/08
[52] U.S. Cl. ........................... 422/1; 49/475.1; 49/477.1; 220/232; 422/296; 422/297; 422/300; 422/307
[58] Field of Search .................................... 422/1, 26, 38, 422/28, 40, 296, 297, 300, 307; 49/475.1, 477.1, 483.1, 504; 220/232, 240

[56] References Cited

U.S. PATENT DOCUMENTS

| | | | |
|---|---|---|---|
| 3,681,008 | 8/1972 | Black | 422/296 X |
| 4,075,787 | 2/1978 | Krahe | 49/477.1 |
| 4,106,661 | 8/1978 | Hunt | 220/232 |
| 4,228,135 | 10/1980 | Wolff | 422/296 |
| 4,335,075 | 6/1982 | Kackos | 422/112 |
| 4,999,165 | 3/1991 | Calabra et al. | 422/113 |
| 5,424,047 | 6/1995 | Zwingenberger et al. | 422/296 |
| 5,446,289 | 8/1995 | Shodeen et al. | 250/455.11 |
| 5,525,295 | 6/1996 | Pflug et al. | 422/27 |
| 5,571,476 | 11/1996 | Newman | 422/26 |

FOREIGN PATENT DOCUMENTS

WO 96/17968  6/1996  WIPO.

*Primary Examiner*—Krisanne Thornton
*Attorney, Agent, or Firm*—Fredrikson & Byron, P.A.

[57] ABSTRACT

A sterilizable passageway for a sterilizable enclosure which includes an enclosure having an outer wall, which has a passageway therethrough. A collar lines a periphery of the passageway, the collar having a sealing surface and a heated surface. A heater is positioned to deliver heat to the heated surface of the collar to selectively heat the collar for sterilization. A selectively positionable door is moveable between an operating position wherein it is spaced away from the passageway to permit the passage of articles into or out of the enclosure and a sterilizing position wherein it substantially seals the passageway. This door optimally includes a gasket positioned to contact the sealing surface of the collar when the door is in its sterilizing position.

10 Claims, 7 Drawing Sheets

FIG. 7

STERILIZABLE PASSAGEWAY

FIELD OF THE INVENTION

The present invention relates to sterilizable manufacturing equipment. More specifically the present invention relates to a sterilizable passageway door having a self-sterilizing inflatable door seal to be used with sterilizable manufacturing equipment.

BACKGROUND OF THE INVENTION

The ability to sterilize, depyrogenate, or otherwise clean manufacturing devices is a desirable feature in many manufacturing environments. (Hereinafter, the words sterile, sterilizable, sterilizing, and sterilization shall also include processes which clean but fall short of full sterilization, e.g. decontamination, as well as processes which exceed the conditions necessary for sterilization, e.g., depyrogenation.) It is often desirable to be able to sterilize various pieces of manufacturing equipment, such as that commonly used in the production of pharmaceuticals, medical devices, and electrical circuit components. Many of these devices include an enclosure which can be sterilized prior to use. This enclosure then provides an ultra-clean environment for the processing of the desired articles. One or more passageways through the enclosure are provided to allow access to the interior of the enclosure so work in process can enter and exit the enclosure. A series of manufacturing devices are sometimes connected via such passageways to form a continuous, sterile path for the processing of the work product.

Whether used as a stand alone apparatus or in a series of devices, these sterilizable enclosures often require periodic sterilization. In order to do this, the enclosures must be able to be effectively sealed from the external environment. Sterilization is usually carried out by employing one or more of irradiation, elevated temperatures, and chemical sterilization.

Often, the process of sealing such enclosures results in a portion of the internal surface of the enclosure being protected from the sterilizing conditions. This most commonly occurs where the enclosure contacts the device (e.g., a door) used to seal the passageway. It is desirable to have an enclosure which has passageways which can be quickly and effectively sterilized even when closed.

SUMMARY OF THE INVENTION

The present invention contemplates both a sterilizable enclosure and a sterilization method. A sterile enclosure of the invention is adapted for periodic sterilization and has an outer wall with a passageway therethrough. A collar lines a periphery of the passageway, the collar having a sealing surface and a heated surface. A heater is positioned to deliver heat to the heated surface of the collar to selectively heat the collar for sterilization. A selectively positionable door is moveable between an operating position and a sterilizing position. In its operating position, the door is spaced away from the passageway to permit the passage of articles into or out of the enclosure. In its sterilizing position, the door substantially seals the passageway. In a preferred embodiment, the door has a gasket positioned to contact the sealing surface of the collar when the door is in its sterilizing position.

In a further embodiment, the sealing surface of the collar extends entirely around the collar's inner surface, the gasket of the door comprising an inflatable seal carried about an external periphery of the door. More preferably, the outer edge of the inflatable seal has an externally extending ridge, the ridge defining a reduced area of sealing contact between the door and the collar when the door is in its sterilizing position.

As noted above, the present invention also contemplates a method of sterilizing an enclosure. This enclosure desirably includes an outer wall with a passageway therethrough; a collar lining a periphery of the passageway, the collar having a sealing surface; and a selectively positionable door moveable between an operating position wherein it is spaced away from the passageway to permit the passage of articles into or out of the enclosure and a sterilizing position wherein it contacts the sealing surface of the collar.

When the door is in its operating position, articles are passed through the passageway in the outer wall. Prior to sterilization, the door is moved into its sterilizing position to substantially seal the passageway. The enclosure is then sterilized while simultaneously heating the collar to a sterilizing temperature for a time sufficient to effectively sterilize the area of contact between the door and the sealing surface of the collar. The door is then moved to its operating position and the collar is allowed to cool to a lower temperature. Thereafter, articles are passed through the passageway in the outer wall.

DETAILED DESCRIPTION OF THE PREFERRED EMBODIMENT

Figure 1:
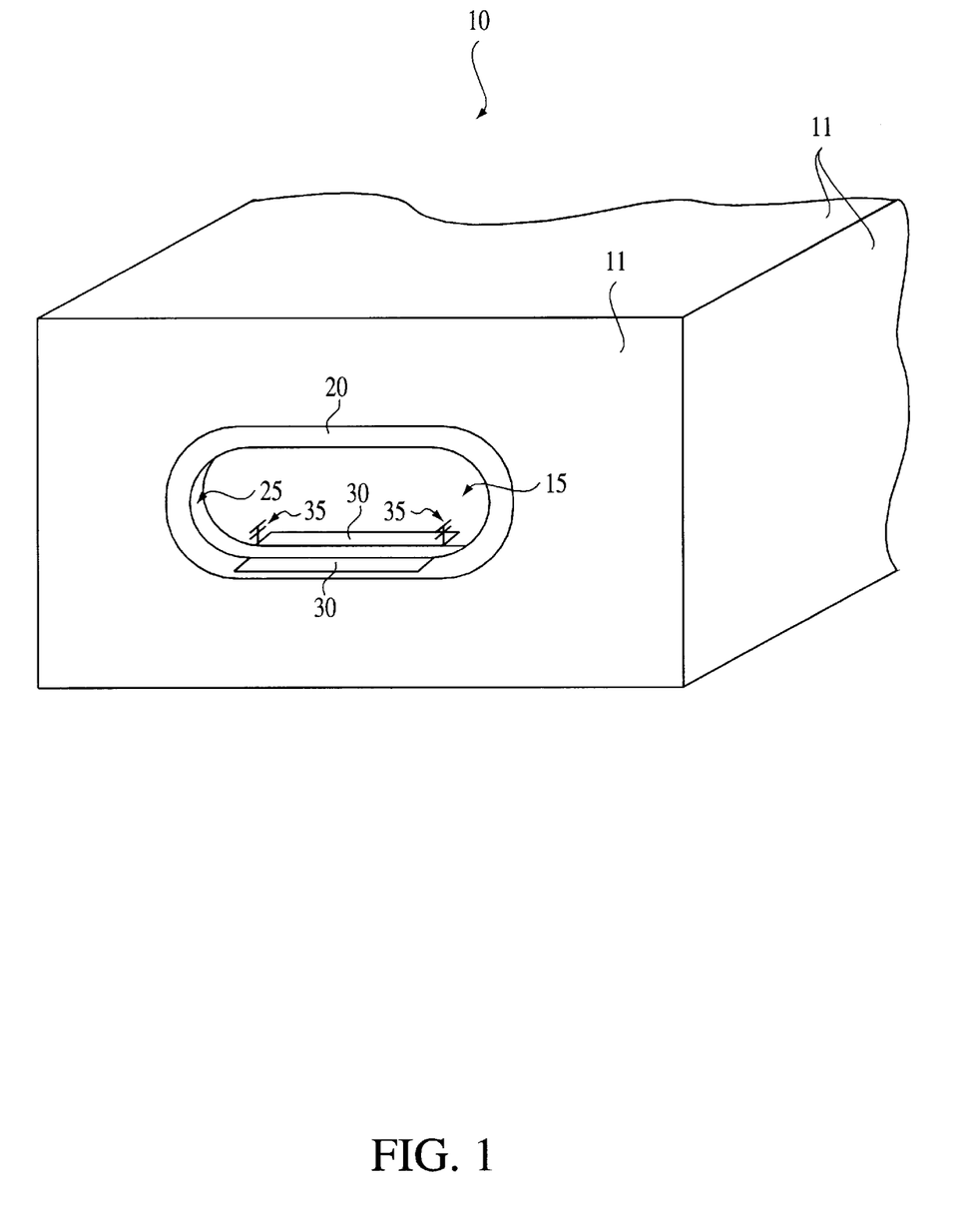
FIG. 1 is a schematic frontal view of an enclosure having a passageway and collar in accordance with one embodiment of the invention.

As seen in FIG. 1, one embodiment of the present invention contemplates an enclosure 10 which is defined by a plurality of outer walls 11. The enclosure is adapted to allow periodic sterilization using known techniques. As noted above, such techniques will commonly include at least one of irradiation, elevated temperatures and chemical sterilization and commonly combines these techniques to maximize effectiveness. One suitable arrangement for sterilizing an enclosure is set forth in U.S. Pat. No. 5,525,295, the teachings of which are incorporated herein by reference.

Figure 2:
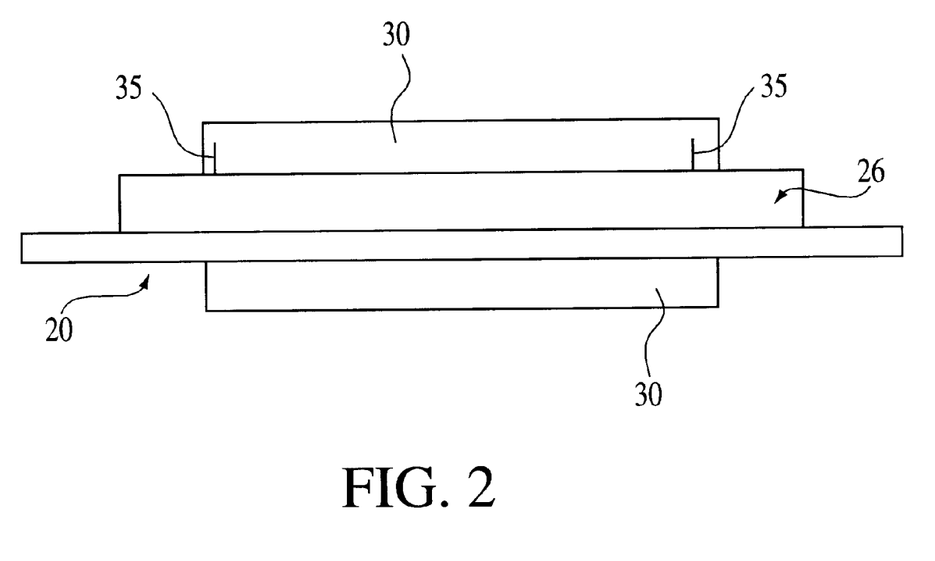
FIG. 2 is a schematic top view of a collar for use in the enclosure of FIG. 1.

An enclosure 10 incorporates one or more passageways 15 which allow articles to be passed into or out of the enclosure for processing within the enclosure. A collar 20 is positioned along the periphery of the passageway 15, this collar 20 having both a sealing surface 25 and a heated surface 26 (best seen in FIG. 2). To facilitate movement of articles into and out of the enclosure 10, a dead plate 30 may be attached to the collar 20. This dead plate may extend outwardly from one side of the passageway or both, and generally is lies along a horizontal plane even with the inner surface of the collar. The dead plate can help support the articles as they are moved through the wall 11. For example, if the enclosure encloses pharmaceutical filling equipment and the filled pharmaceutical containers are moved from this enclosure to a second enclosure for sealing, the dead plate can physically support the filled pharmaceutical containers as they move from one enclosure to the next.

To facilitate the orderly passage of articles over the dead plate 30 through the passageway 15, one or more rails 35 can be attached to the dead plate 30 or collar 20. These rails may serve to guide the articles so they will be presented to automated equipment on the opposite side of the outer wall 11 in a predictable position. For reasons made more clear below, these rails 35 may be retracted within the enclosure prior to sealing the passageway 15. This can be accomplished in a variety of ways. The rails may be attached to the dead plate and the dead plate can be mounted on a moveable armature so the entire plate can be moved from a position adjacent the passageway (as shown) to a position wherein it is positioned away from the passageway (not shown). Depending on the relative positions of the rails and the moveable door described below, it may be possible simply to pivot the dead plate about a hinge positioned adjacent the passageway 15.

The present invention also includes a selectably positionable door 40 which can be moved between an open position and a sterilizing position. In its open position, the door 40 is sufficiently spaced away from the passageway to permit the free passage of articles into or out of the enclosure through the passageway. In its sterilizing position, the door 40 substantially seals the passageway. In one embodiment, the door 40 is substantially hollow. This feature provides for a lightweight door 40 to facilitate moving the door from its open position to its sterilizing position.

Figure 3:
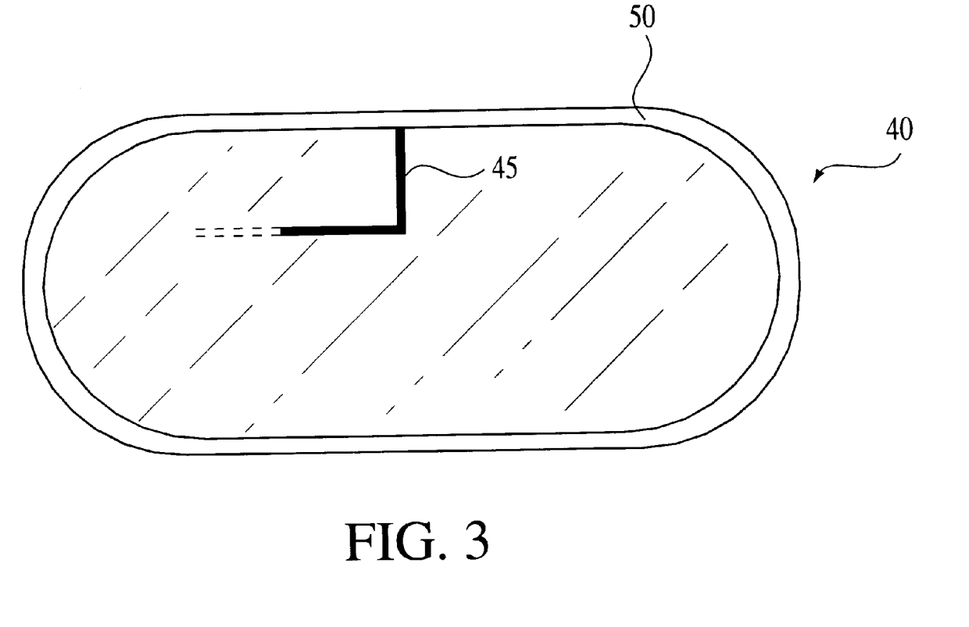
FIG. 3 is a schematic frontal view of a door for use in connection with the collar of FIG. 2.
Figure 4:
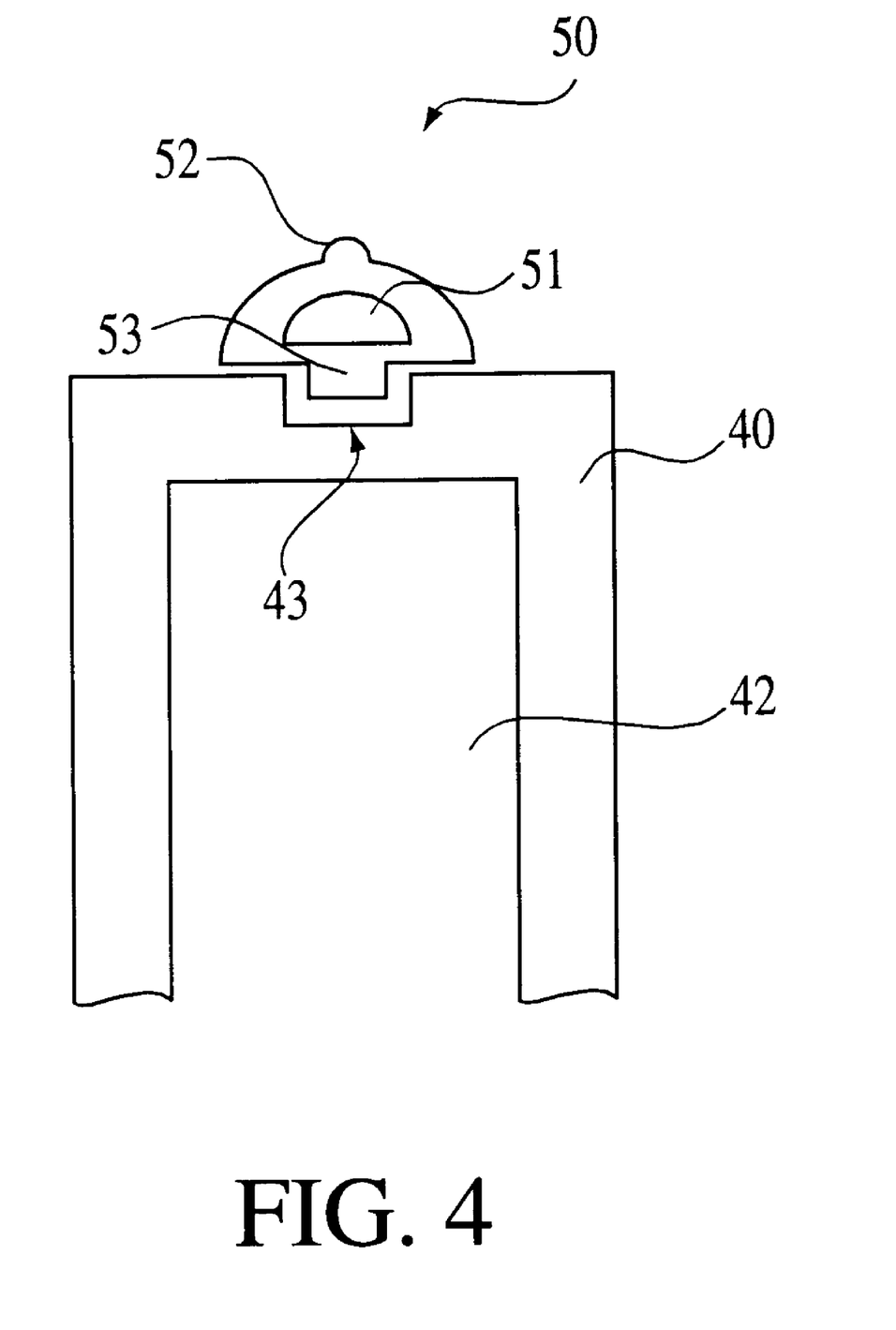
FIG. 4 is a schematic, cross sectional view of a portion of the door of FIG. 3.

In the embodiment illustrated in FIGS. 3 and 4, the door includes a gasket 50 extending about its periphery. This gasket is used to better seal the door 40 against the collar 20 to substantially seal the passageway 15. When the door 40 is in its sealing position, this gasket 50 comes into sealing contact with the sealing surface 25 of the collar. In a preferred embodiment, this gasket 50 comprises an inflatable seal, such as an inflatable O-ring seal.

The gasket 50 may be made of any suitably resilient material which facilitates the substantial sealing of passageway 15. Obviously, the material for gasket 50 should be capable of withstanding the sterilizing conditions used to sterilize the enclosure and the sealing surface 25 of the collar. If sterilization is to be carried out using high temperatures, the gasket should be capable of withstanding the expected temperatures without critical degradation of its properties. If chemical sterilization is employed, the gasket material should be able to withstand the attack of such sterilization agents over a number of cycles. One material which has been found suitable for the gasket is fabric reinforced silicone rubber with a polymer classification of ASTM D-1418; VMQ. This material will provide a resilient, inflatable O-ring gasket that can withstand repeated cycling through a sterilization routine that involves both elevated temperatures and chemical atack by a steam and peroxide sterilant.

For those embodiments which incorporate an inflatable gasket 50, a gas hose 45 may be run to the substantially open area inside door 40. This gas hose 45 will supply pressurized gas for the inflation of inflatable seal 50. Any number of gases can be used to inflate the seal. Most commonly, this will be HEPA filtered compressed air; however, in specialized environments, a non-reactive gas, such as nitrogen ($N^2$) or a noble gas, may be desired.

FIG. 4 shows a cross section of one particularly preferred inflatable gasket 50 attached to the door 40. The gasket can be provided with an inwardly-extending gasket tab 53 which is seated in a peripheral gasket receiving recess 43. If so desired, the gasket can be further secured within this recess 43 by means of a suitable adhesive.

FIG. 4 shows that the inflatable gasket 50 has an internal chamber 51. The inflation gas mentioned above would be delivered to or vented from this chamber 51 through the gas hose (45 in FIG. 3) to selectively inflate or deflate the gasket during use.

The illustrated gasket also includes an externally extending ridge 52 which protrudes peripherally outwardly from the rest of the gasket. As explained below in connection with FIG. 6, this ridge helps minimize the contact area between the gasket 40 yet provide a suitable seal between these components to substantially seal the enclosure. In the illustrated embodiment, the gasket has a generally D-shaped cross section, with the outer surface of the gasket tapering downwardly away from either side of the ridge 52. This will help further ensure that the contact area is minimized even if the gasket is over inflated or the door is slightly mispositioned with respect to the collar.

Figure 5:
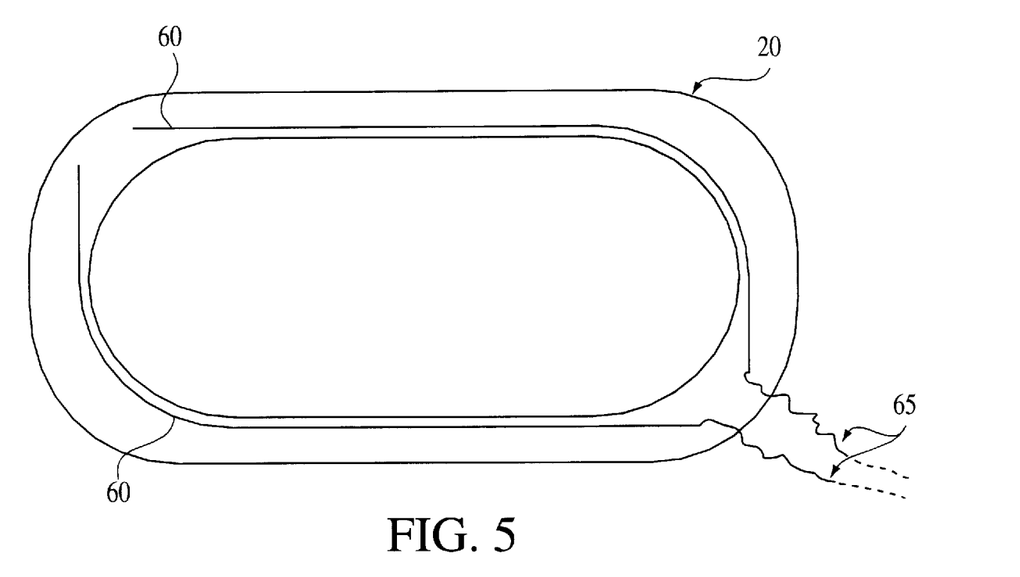
FIG. 5 is a schematic rear view of the collar of FIG. 2.

As best seen in FIG. 5, the heating surface 26 of the collar 20 is operatively connected to a heater. While a conduit for circulating heated air or any other suitable heat supply could be used, the illustrated device employs a heating element 60 which is in direct physical contact with an external heated surface 26 of the collar. This heating element 60 may be one continuous element, or several independent heating elements which together deliver heat to the heated surface 26 of the collar. One preferred heating element is a resistance heater, with current supplied via wires 65 for selectively heating the element and, in turn, the collar.

The heating surface 26 should be adapted to deliver heat from the heater to the sealing surface 25 of the collar so the sealing surface may be heat sterilized, as described below. Most commonly, the collar will be formed of a heat-conductive material (e.g. stainless steel) and will itself conduct sufficient heat from the heating element 60 to the sealing surface 25 for adequate sterilization of both the sealing surface 25 and the portion of the gasket 50 which contacts the sealing surface 25.

Figure 6:
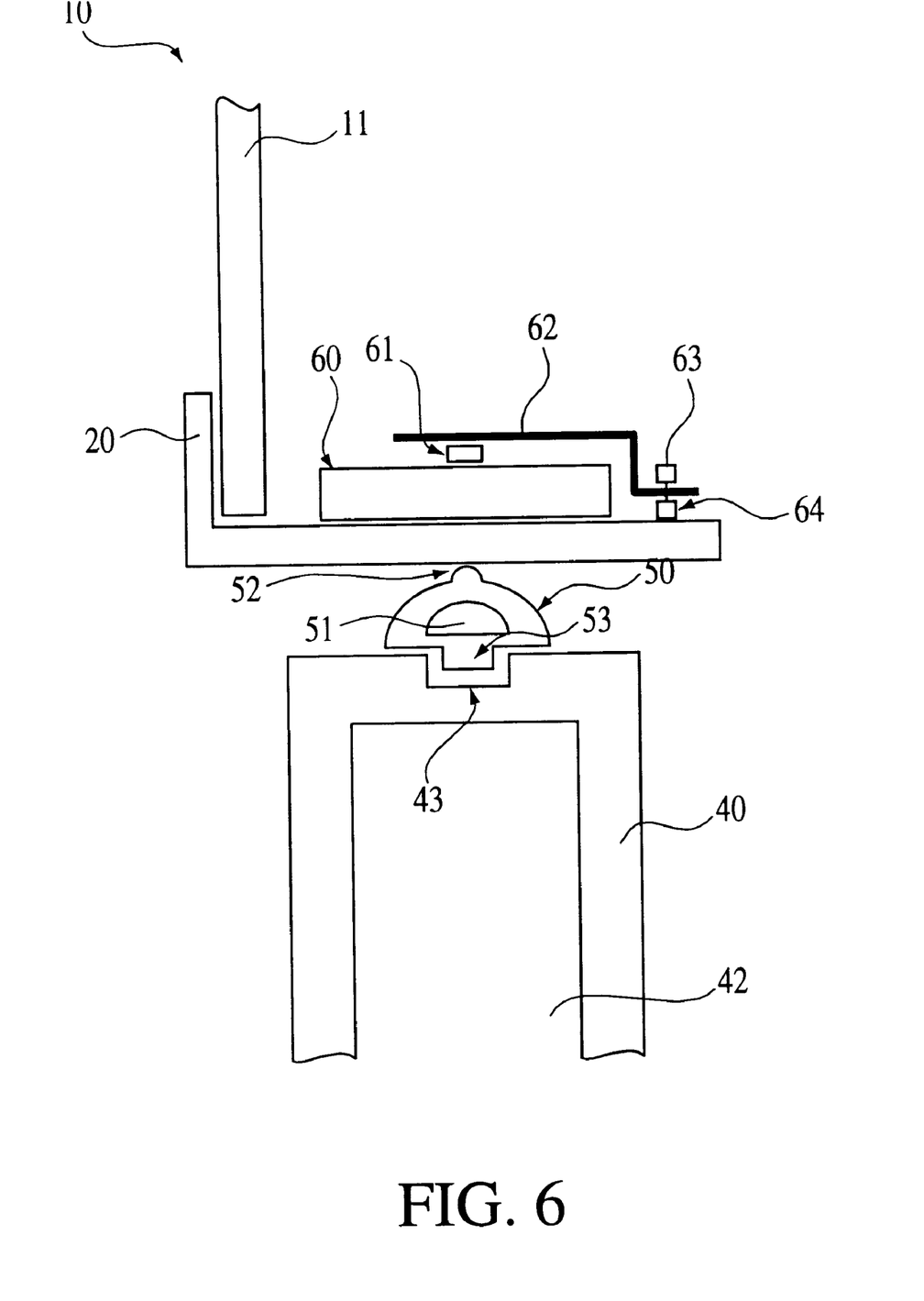
FIG. 6 is a schematic, cross sectional view similar to FIG. 4 showing engagement between the door and the collar.

FIG. 6 illustrates the door of FIG. 4 in its sterilizing position. In this position, the externally extending ridge 52 of the gasket 50 contacts a relatively small portion of the sealing surface 25 of the collar. By heating the heating surface 26 of the collar with the heating element 60, both the sealing surface 25 and the portion of the externally extending ridge 52 in contact therewith can be heated to a temperature suitable for sterilization. That portion of the gasket 50 which is exposed to the interior of the enclosure 10 will be subjected to essentially the same sterilizing conditions as the rest of the enclosure, sterilizing that surface of the gasket. As a consequence, one can sterilize not only the enclosure itself, but also the exposed sealing surface of the collar 20 and the area of contact between the door and the collar. This prevents the area of contact between the door and the collar from perennially harboring pathogens despite repeated sterilization, which is a problem which has afflicted prior art designs.

In the illustrated embodiment, the heating element 60 can be attached to the collar 20 by a heater clip 61. In order to reduce the transfer of heat from the heater 60 to the clip 61, an insulator 62 can be positioned between the heater 60 and the heater clip 61. The heater clip 61 secures the heater 60 in direct physical contact with the heated surface 26 of the collar via a fastener 63. In a preferred embodiment, a spacer 64 will be used to position the heater clip 61 away from the collar 20. Other ways of attaching the heater 60 to the heated surface 26 will be readily apparent to those skilled in the art.

Figure 7:
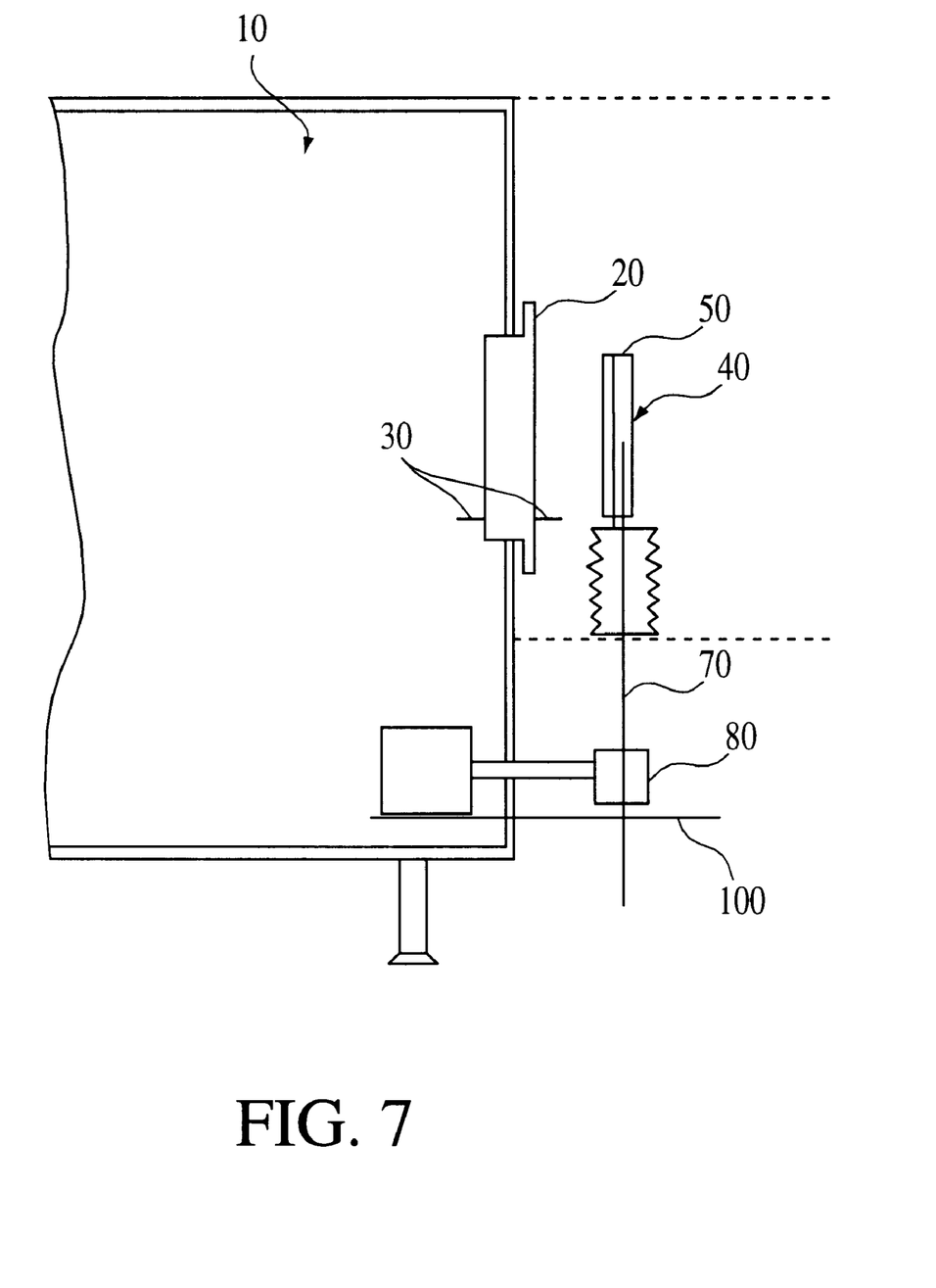
FIG. 7 is a schematic, cross sectional view of the enclosure of FIG. 1.

As noted above, the door 40 is desirably selectively moveable between an operating position and a sterilizing position. One of the many ways of carrying out this movement is shown in FIG. 7. Here, the door 40 is attached to a vertical control rod 70. This control rod 70 may be moved vertically up and down by means of an electrical motor 80, e.g., by means of a screw drive mechanism. This control rod 70 may also be moved horizontally, such as by mounting the rod 70 and motor 80 on a horizontally moveable base 100. In this arrangement, one would move the door into its sterilizing position by moving the door downwardly using the control rod 70 then, once the door is horizontally aligned with the opening in the collar, it will be moved horizontally to position the gasket 50 adjacent the sealing surface of the collar. One can move the door back to its operating position be reversing these steps. Obviously, a wide variety of mechanical systems could be used to selectively position the door for operation in accordance with the invention.

The present invention also contemplates a method of sterilizing an enclosure. In the ensuing discussion, reference will be made to the design illustrated in FIG. 1–7 and discussed above. It should be understood, however, that the method of the invention can be practiced using devices which differ significantly from the specific embodiment outlined above and that the following discussion should not be limited to such a specific structure.

In normal operation of the enclosure, articles will be passed through a passageway 15 in the outer wall 11. Such articles can include a wide range of pharmaceuticals, medical products and other products where a sterile manufacturing environment is important. During this normal operation, the door 40 will be in its operating position. (In the embodiment of FIG. 7, this would be generally above the passageway, but any position wherein the door is spaced away from the passageway sufficiently to permit work in process to be passed through the passageway without interference will suffice.)

When it is desired to sterilize the enclosure, the door 40 will be moved to its sterilizing position. As noted above, when the door is in its sterilizing position, it substantially seals the passageway 15. In the illustrated embodiment, the door 40 may be will be positioned within the collar 20 such that the gasket 50 of the door is positioned adjacent the sealing surface 25 of the collar. The gasket can then be inflated through gas hose 45 until the externally extending ridge 52 sealingly engages the sealing surface 26 of the collar.

The enclosure 11 can then be sterilized. As noted above, it is not necessary that the enclosure be fully sterilized; it need only be sufficiently depyrogenated or otherwise cleaned to provide an environment in the enclosure conducive to the operations for which the enclosure is intended. If one is handling pharmaceutical products in the enclosure, for example, class 100 sterilization or better may be necessary. If non-medical devices were being handled instead, though, it may not be necessary to fully sterilize the enclosure. Such sterilization can be carried out through irradiation, heating, chemical sterilization, or any other sterilizing methodology known in the art.

Preferably at the same time that the enclosure is being sterilized, the collar 20 can be heated with the heating element 60 to a sterilizing temperature for a time sufficient to effectively sterilize the area of contact between the gasket 50 of the door 40 and the sealing surface 25 of the collar 20. For example, a sterilizing temperature of between about 170° C. and about 250° C. maintained for a time between about thirty minutes and about sixty minutes has been found to work well. As with the sterilization of the enclosure, though, particular applications may require more or less rigorous sterilization.

Thereafter, the door 40 can be returned to its operating position. The collar 20 is allowed to cool to a lower temperature than that reached for sterilization. Desirably this temperature would be less than 40° C. but, again, this will depend on the sterilization temperature required and the susceptibility of the work in process to excess heat. The collar can be allowed to cool, in whole or in part, with the door in its sterilizing position. In most circumstances, though, it will be advantageous to move the door to its operating position to increase the exposed surface area of the collar and the door to promote cooling. Once the collar and/or the door have sufficiently cooled to preclude damage to the work in process moving through the passageway 15, normal operation can again resume and articles may passed through the passageway 15.

As noted above, a plurality of rails 35 may be utilized to help guide articles through the passageway. Such rails may obstruct smooth movement of the door, either forcing the door to move along an unnecessarily complex path from its operating position to its sterilization position. If the rails extend through the passageway over the sealing surface 25 of the collar, though, the rails could completely preclude the door from properly sealing the enclosure. Accordingly, a further embodiment of a method of the invention includes the step of retracting one or more rails prior to the step of moving the door to its sterilizing position. The movement of these rails can be accomplished by any suitable means, as noted above.

While several preferred embodiments of the present invention have been described, it should be understood that various changes, adaptations and modifications may be made therein without departing from the spirit of the invention and the scope of the appended claims.

What is claimed is:

1. A sterilizable enclosure adapted for periodic sterilization, comprising:

a. an outer wall having a passageway therethrough;

b. a collar lining a periphery of the passageway, the collar having a sealing surface and a heated surface;

c. a heater positioned to deliver heat to the heated surface of the collar to selectively heat the collar for sterilization; and d. a selectively positionable door moveable between an operating position wherein it is spaced away from the passageway to permit the passage of articles into or out of the enclosure and a sterilizing position wherein it substantially seals the passageway, the door having a gasket positioned to contact the sealing surface of the collar when the door is in its sterilizing position.

2. The device of claim 1 wherein the sealing surface of the collar extends entirely around the collar's inner surface, the gasket of the door comprising an inflatable seal carried about an external periphery of the door.

3. The device of claim 2 wherein the outer edge of the inflatable seal has an externally extending ridge, the ridge defining a reduced area of sealing contact between the door and the collar when the door is in its sterilizing position.

4. The device of claim 2 wherein the inflatable seal is made of a substantially nonporous material which is stable at temperatures in excess of 250° C.

5. The device of claim 2 wherein the heater is a resistance heater.

6. The device of claim 2 wherein the inflatable seal is an inflatable O-Ring seal.

7. The device of claim 2 further comprising a plurality of rails positioned to extend through said passageway for the purpose of guiding articles through the passageway when the door is in its operating position, the rails being adapted to retract within the enclosure when the door is moved to its sterilizing position.

8. A method of sterilizing, comprising:
   a. providing an enclosure having an outer wall with a passageway therethrough; a collar lining a periphery of the passageway, the collar having a sealing surface; and a selectively positionable door moveable between an operating position wherein it is spaced away from the passageway to permit the passage of articles into or out of the enclosure and a sterilizing position wherein it contacts the sealing surface of the collar;
   b. with the door in its operating position, passing articles through the passageway in the outer wall;
   c. moving the door into its sterilizing position to substantially seal the passageway;
   d. sterilizing the enclosure while simultaneously heating the collar to a sterilizing temperature for a time sufficient to effectively sterilize the area of contact between the door and the sealing surface of the collar;
   e. moving the door to its operating position and allowing the collar to cool to a lower temperature;
   f. thereafter, passing articles through the passageway in the outer wall.

9. The method of claim 8 wherein the door further comprises a gasket having an inflatable seal, the step of moving the door into its sterilizing position comprising positioning the door within the passageway and inflating the seal to bring the gasket into sealing engagement with the sealing surface of the collar.

10. The method of claim 9 wherein the enclosure further comprises a plurality of rails positioned to extend through said passageway for the purpose of guiding articles through the passageway when the door is in its operating position, the method further comprising retracting the rails out of the passageway prior to moving the door to its sterilizing position.

* * * * *